US008947102B1

(12) United States Patent
Evett et al.

(10) Patent No.: US 8,947,102 B1
(45) Date of Patent: Feb. 3, 2015

(54) SOIL WATER AND CONDUCTIVITY SENSING SYSTEM

(75) Inventors: Steven R. Evett, Amarillo, TX (US); Scott K. Anderson, Meridian, ID (US); Joaquin J. Casanova, Amarillo, TX (US); Robert C. Schwartz, Bushland, TX (US)

(73) Assignee: The United States of America as represented by the Secretary of Agriculture, Washington, DC (US)

( * ) Notice: Subject to any disclaimer, the term of this patent is extended or adjusted under 35 U.S.C. 154(b) by 338 days.

(21) Appl. No.: 13/404,491

(22) Filed: Feb. 24, 2012

Related U.S. Application Data

(60) Provisional application No. 61/515,381, filed on Aug. 5, 2011.

(51) Int. Cl.
*G01R 27/04* (2006.01)
(52) U.S. Cl.
USPC ............................ 324/629; 324/634; 324/600
(58) Field of Classification Search
USPC ................. 324/600, 629–643, 664, 689, 694, 324/76.11–76.12, 250, 754.06, 200
See application file for complete search history.

(56) References Cited

U.S. PATENT DOCUMENTS

| 5,539,637 | A | | 7/1996 | Upchurch et al. |
| 5,570,030 | A | * | 10/1996 | Wightman ..................... 324/694 |
| 6,016,971 | A | * | 1/2000 | Welch et al. .................... 239/63 |
| 2009/0277506 | A1 | | 11/2009 | Bradbury et al. |

OTHER PUBLICATIONS

Jackson, Ray D., et al., "A Reexamination of the Crop Water Stress Index", Irrigation Science, 1988, 9, pp. 309-317.
Peters, D. Troy, et al., "Modeling Diurnal Canopy Temperature Dynamics Using One-Time-of-Day Measurements and a Reference Temperature Curve", Agronomy Journal, vol. 96, Nov.-Dec. 2004, pp. 1553-1561.
O'Shaughnessy, Susan A., et al., "Soil Water Measurement and Thermal Indices for Center Pivot Irrigation Scheduling" presented at Proc. Irrigation Assoc. Show, 2008.
O'Shaughnessy, Susan A., et al., "Automatic Irrigation Scheduling of Grain Sorghum Using a CWSI and Time Threshold", An ASABE Conference Presentation, Paper Number: IRR10-9011, written for presentation at the 5th National Decennial Irrigation Conference, Phoenix, AZ on Dec. 5-8, 2010.
O'Shaughnessy, Susan A., et al., "Integration of Wireless Sensor Networks into Moving Irrigation Systems for Automatic Irrigation Scheduling", An ASABE Meeting Presentation, Paper Number: 083452, written for presentation at the 2008 ASABE Annual Meeting on Jun. 29-Jul. 2, 2008, Providence, RI.

(Continued)

*Primary Examiner* — Melissa Koval
*Assistant Examiner* — Trung Nguyen
(74) *Attorney, Agent, or Firm* — John D. Fado; Robert D. Jones; Lesley Shaw

(57) ABSTRACT

Soil water content and bulk electrical conductivity may be determined by time domain reflectometry at multiple depths in the soil such that the entire soil profile from the surface to a user-selected depth may be characterized. A short rise-time pulse is passed into an electrode and the reflected pulse is captured at multiple times. A waveform of reflection coefficient versus time is determined, which may be used to determine the pulse travel time, effective frequency and reflection coefficients at times necessary for the determination of the soil water content and bulk electrical conductivity.

13 Claims, 8 Drawing Sheets

(56) References Cited

OTHER PUBLICATIONS

Peters, R. T., et al., "Spatial and Temporal Analysis of Crop Conditions Using Multiple Canopy Temperature Maps Created With Center-Pivot-Mounted Infrared Thermometers", Transactions of the ASABE, 2007, vol. 50 (3), pp. 919-927.

Hunsaker, Douglas J., et al., "Estimating cotton evapotranspiration crop coefficients with a multispectral vegetation index", Irrigation Science, 2003, 22, pp. 95-104.

Hunsaker, D. J., et al., "Cotton Irrigation Scheduling Using Remotely Sensed and FAO-56 Basal Crop Coefficients", Transactions of the ASAE, 2005, vol. 48, 4, pp. 1395-1407.

Peters, R. Troy, et al., "Automation of a Center Pivot Using the Temperature-Time-Threshold Method of Irrigation Scheduling", Journal of Irrigation and Drainage Engineering, May/Jun. 2008, pp. 286-291.

Evett, Steven R., et al., "Controlling Water Use Efficiency with Irrigation Automation: Cases from Drip and Center Pivot Irrigation of Corn and Soybean", Southern Conservation Systems Conference, Amarillo, TX Jun. 26-28, 2006, pp. 57-66.

\* cited by examiner

SOIL WATER AND CONDUCTIVITY SENSING SYSTEM

This application claims the benefit under 35 U.S.C. 1.19(e) of U.S. provisional No. 61/515,381, filed Aug. 5, 2011, the contents of which are incorporated by reference herein.

BACKGROUND OF THE INVENTION

1. Field of the Invention

The invention is drawn to a method and apparatus for sensing the soil water content and soil bulk electrical conductivity (BEC). Moreover, the water content and BEC may be determined to arbitrary depths in discrete intervals for managing the irrigation of plants, studying and managing environmental interventions and any other applications.

2. Description of the Prior Art

Soil water content and bulk electrical conductivity have both been sensed by electronic systems that measure the electrical response to an imposed electromagnetic (EM) signal. Such systems differ in the nature of the imposed EM signal, the nature of the measured electrical response, and the nature of the electronic circuitry used and its ability to measure various aspects of the electrical response. Three main measurement paradigms exist; those based on capacitance, those based on time domain transmission measurements; and those based on time domain reflectometry.

Systems known as capacitance systems impose an oscillating sinusoidal electrical wave to one or more pairs of electrodes, using one of many possible oscillator circuits, and measure the resonant frequency at which the electronic oscillator system stabilizes. Each pair of electrodes constitutes a capacitor which is part of the oscillator circuit. The electrodes may or may not be in contact with the soil, but if not in contact, then the electrodes are close enough to the soil that the fringing EM field of the capacitor (electrode pair) invades the soil to some extent. Either arrangement makes the soil medium part of the dielectric material involved in the capacitor formed by the electrodes. The capacitance of said capacitor is a function of the electrode geometry and the dielectric permittivity of the medium invaded by the EM field the capacitor. As the soil water content increases the dielectric permittivity of said medium increases and the frequency of oscillation decreases. Calibration against water content may be in terms of frequency, scaled frequency, or some quantity derived through a theoretical transformation such as the permittivity. Although earlier examples exist, the design of Dean et al. (1987, Soil moisture measurement by an improved capacitance technique: Part I. Sensor design and performance. J. Hydrol. 93:67-78) was the prototype for many existing capacitance systems that are deployed as electrode pairs inside a plastic access tube installed in the soil such that the fringing field invades the soil surrounding the access tube.

The down-hole capacitance sensors all employ a capacitive sensor consisting of two cylindrical electrodes arranged along a common axis and separated by a space that is typically filled with a plastic. This arrangement is placed in an access tube composed of some sort of plastic or plastic-fiberglass composite, which itself is inserted into the soil. The electrodes are connected to an oscillating circuit that settles to a resonant frequency that will change it the dielectric properties of the soil material around the access tube change. Since the two electrodes are in the access tube, most of the EM field developed between the electrodes is itself confined to within the access tube. Only a small part of the EM energy, called the fringing field, enters and interacts with the soil. The volume of soil penetrated by the EM field is static, although we now know that its exact shape and volume are dependent on the arrangement of the resistive and capacitive elements of the soil outside the access tube. The capacitance of the soil-access tube system, C (F), is given by (Dean et al., 1987, ibid):

$$C = g \in_a \in_o \quad [1]$$

where $\in_a$ is the system apparent relative permittivity (-), $\in_o$ is the permittivity of free space (F/m) and the geometric constant, g (m), has a value dependant on the geometry of the system. The resonant frequency, F (Hz), is given by (Dean et al., 1987):

$$F = [2\pi(L)^{0.5}]^{-1}(C^{-1} + C_b^{-1} + C_c^{-1})^{0.5} \quad [2]$$

where $C_b$ and $C_c$ are the electrode capacitances including the capacitances of internal circuit elements to which the electrodes are connected, C is the capacitance of the soil-access tube system defined in Eq. [1], and L is the inductance (henries) of the coil in the LC oscillating circuit. As soil water content increases, C increases in concert with the increasing soil apparent permittivity, and F decreases.

Multiple field and laboratory studies have shown that capacitance sensors used in access tubes were much less well correlated with field measured water contents than was the neutron probe (Evett and Steiner, 1995, Precision of neutron scattering and capacitance type soil water content gauges from field calibration. Soil Sci. Soc. Amer. J., vol. 59, pp. 961-968; Evett et al., 2006, Soil profile water content determination: Sensor accuracy, axial response, calibration, temperature dependence and precision. Vadose Zone J. 5:894-907; Evett et al., 2009, Soil profile water content determination: Spatiotemporal variability of electromagnetic and neutron probe sensors in access tubes. Vadose Zone J. 8(4):926-941; and Mazahrih et al., 2008, Field Calibration Accuracy and Utility of Four Down-Hole Water Content Sensors, Vadose Zone Journal, vol. 7, no. 3, p. 992). Also, standard deviations of profile soil water content determined by capacitance sensors and by a down-hole quasi-TDR sensor were larger than those determined using the neutron probe or gravimetric sampling by hydraulic push probe, so much so that numbers of access tubes and sensors required to obtain reasonable field mean profile water contents was unaffordable. In every case, the standard deviation increased in drier soil with obvious implications for use of soil water sensors in regulated deficit irrigation management. Many of the results of the multi-national IAEA study were published in a guide to field estimation of soil water content (Evett et al., 2008, Field Estimation of Soil Water Content: A Practical Guide to Methods, Instrumentation, and Sensor Technology. 131 pp. IAEA-TCS-30. International Atomic Energy Agency, Vienna, Austria. ISSN 1018-5518).

The capacitance sensors, though relatively poorly correlated with field measured soil water content, were very well self-correlated when measurements at the same depth and access tube were compared amongst sensors (Evett and Steiner, 1995, ibid; Evett et al., 2009, ibid). This indicated that capacitance sensors responded to some property of the soil-water system around the access tube that was not water content alone. Evett and Steiner (1995, ibid) hypothesized that this property was related to soil structure and non-uniform penetration into the soil of the EM field of the sensor. Studies of EM field penetration in heterogeneous materials showed over estimation of permittivity and uneven EM field penetration in those materials (e.g., Panteny et al., 2005 The frequency dependent permittivity and AC conductivity of random electrical networks. Ferroelectrics 319:199-208), supporting the inference that the EM field from a capacitance sensor is distorted by the individual arrangement of soil peds and pattern of water content in the peds around each access tube at each depth rather than being responsive to the mean water content of the soil around each access tube at each depth. This means that the geometric constant (fundamental to capacitance measurement theory) changes according to the small scale heterogeneity of soil properties at each measurement depth and access tube, which results in a different resonant frequency and water content estimate even if mean water content around the access tube is the same. Using a different EM sensor, Logsdon (2009, CS616 calibration: Field versus laboratory. Soil Sci. Soc. Am. J. 73:1-6) confirmed that uneven water contents in proximity to the sensor caused the sensor to overestimate water content. Several field studies have shown that capacitance and quasi-TDR sensors exhibit unrealistic spatial variability when compared with NP and volumetric gravimetric sampling (Evett et al., 2009, ibid; Heng et al., 2002, Comparison of soil moisture sensors between neutron probe, Diviner 2000 and TDR under tomato crops. Pp. 1532-1-1532-9 In Proc. $17^{th}$ World Cong. Soil Sci., 14-21 August, Bangkok, Thailand).

Laboratory calibrations of capacitance sensors typically exhibit less accuracy than those from the NP or TDR. Calibrations were conducted in large soil columns (three replicates each of ground, sieved and repacked soil from the Ap, Bt, and calcic Bt horizons) by Evett et al. (2006, ibid). Calibration accuracy ranged from 0.018 to 0.058 $m^3$ $m^{-3}$ (RMSE of regression), comparable to values reported by Baumhardt et al. (2000, Soil material, temperature, and salinity effects on calibration of multisensor capacitance probes. Soil Sci. Soc. Amer. J. 64(6)1940-1946) and Paltineanu and Starr (1997, Real-time soil water dynamics using multisensor capacitance probes: Laboratory calibration. Soil Sci. Soc. Am. J. 61:1576-1585) for laboratory calibrations, but larger than the calibration accuracy of ≤0.01 $m^3$ $m^{-3}$ for conventional TDR and NP in the same study. Except for conventional TDR, laboratory calibrations did not, however, provide accurate soil water contents when used in the field (Evett et al., 2009, ibid). In the field, water contents were overestimated on the wet end and underestimated on the dry end; and values of change in profile water storage were relatively inaccurate for the capacitance sensors when compared with NP or gravimetric sampling. Subsequently, field calibrations of the NP and three capacitance sensor systems were conducted at the West Side Field Station in the San Joaquin Valley, Calif. (Mazahrih et al., 2008, ibid). Calibrations for the NP had high accuracy compared with those from the three capacitance sensors; and only three separate calibrations were needed to cover the 2-m deep profile over which the NP was calibrated. Also, the calibration for the depth range from 26 to 114 cm was only slightly different from that for the 131 to 201 cm depth range. In contrast, calibrations for the capacitance sensors were affected by increasing bulk electrical conductivity with depth, despite the fact that the sweet pepper crop in the drip irrigated field showed no salinity symptoms. Capacitance sensor calibration slopes increased strongly with depth; and the sensor frequency response to increasing water content became very small as depth increased, making the sensor output highly variable. Since the profile pattern of bulk electrical conductivity is expected to vary greatly across the field and with time (e.g., Burt et al., 2003, Long-term salinity buildup on Drip/Micro irrigated trees in California. In "Understanding & Addressing Conservation and Recycled Water Irrigation", Proceedings of the International Irrigation Association Technical Conference. Pp. 46-56. November 2003; Hanson et al., 2003, Drip irrigation in salt affected soil. In "Understanding & Addressing Conservation and Recycled Water Irrigation", Proceedings of the International Irrigation Association Technical Conference. Pp. 57-65. November 2003), these calibrations are essentially unusable for accurate soil water content estimation using the capacitance sensors.

Other examples of calibration errors increasing with soil bulk electrical conductivity were given by Baumhardt et al. (2000, ibid) and Evett and Schwartz (2009, Comments on "J. Vera et al., Soil water balance trial involving capacitance and neutron probe measurements". Agric. Water Manage. 96:905-911). Geesing et al. (2004, Field calibration of a capacitance soil water probe in heterogeneous fields. Aust. J. Soil Res. 42:289-299) reported RMSE values of 0.03 to 0.04 $m^3$ $m^{-3}$ for field calibrations of the Diviner 2000 in loam and silt loam soils, respectively; and demonstrated the necessity of soil-specific calibration as have other authors (Baumhardt et al., 2000, ibid). For field calibrations at two sites, Polyakov et al. (2005, Calibration of a capacitance system for measuring water content of tropical soil. Vadose Zone J. 4:1004-1010) reported RMSE=0.031 and 0.048 $m^3$ $m^{-3}$ for calibration of a capacitance sensor system (EasyAg 50, Sentek, Pty., Ltd., Stepney, South Australia) in a kaolinitic silty clay loam in Hawaii. Although soil classification was the same, calibrations for the two sites (one was a hillslope and the other a nearby cultivated terrace) were clearly different. A laboratory calibration for the same soil using re-packed soil columns resulted in RMSE=0.039 $m^3$ $m^{-3}$. Results with capacitance sensors have tended to be better in sandy soils for which calibration coefficients tend to be similar (Robinson, 2001, Comments on "Field calibration of a capacitance water content probe in fine sand soils". Soil Sci. Soc. Am. J. 65(5): 1570-1571). However, sandy soils tend to have field capacity water contents <0.10 $m^3$ $m^{-3}$ (Morgan et al., 1999, Field calibration of a capacitance water content probe in fine sand soils. Soil Sci. Soc. Am. J. 63:987-989) and available water holding capacities of <0.04 $m^3$ $m^{-3}$, which places great demands on accuracy. Although Morgan et al. (1999, ibid) reported an RMSE of calibration of 0.0085 $m^3$ $m^{-3}$, other calibration studies have reported larger values for coarse textured soils. For example, data from a sandy to sandy loam soil in California resulted in RMSE=0.031 $m^3$ $m^{-3}$; and data from a loamy sand to sandy loam soil in Australia resulted in RMSE=0.016 $m^3$ $m^{-3}$ (Paltineanu and Starr, 1997, ibid). Both were laboratory calibrations using re-packed soil columns.

Existing capacitance systems are plagued by several problems. Oscillator frequency is dependent on water content; but, in the frequency range employed by these sensors, the permittivity is dependent on frequency; the result being a system with two unknowns but a single measurement. In the frequency range employed by capacitance sensors, the permittivity is also strongly influenced by the soil BEC and by the soil bound water content. Bound water is water so close to soil particle surfaces that the free rotation of the water molecule in an oscillating EM field is inhibited, changing the permittivity of the soil water system. The strength of the fringing field and the extent to which the EM field invades the soil outside the access tube is inversely proportional to the frequency, so attempts to avoid problems related to low frequencies are thwarted by the insensitivity of the measurement system that arises from using higher frequencies. The EM field invades a uniform medium with a well defined shape, but soil is highly structured and often does not act like a uniform medium at the EM frequencies used in capacitance sensors. In particular, the EM field preferentially invades more conductive soil volumes. Since the arrangement of soil structural elements around an access tube changes with location and depth in ways that are not predictable, a priori, the resonant frequency of the capacitance system is influenced by the closeness and arrangement of more conductive soil volumes. Soil BEC is a strong function of soil water content, meaning that soil water content variations at small scales near access tubes will impose small scale variations in soil BEC which will induce variations in EM field penetration into the soil and in frequency response of capacitance systems even if the larger scale soil volumetric water content is identical between two different realizations of the soil structure. Both soil BEC and bound water are strongly dependent on soil temperature, meaning that capacitance systems are temperature dependent, usually more so at larger soil water contents. Although at least one capacitance system now includes circuitry to measure soil BEC independently, no system exists that is free of temperature effects.

Both time domain reflectometry (TDR) and time domain transmission (TDT) systems attempt to measure the speed at which an electronic pulse transits an electrode that is in contact with the soil. Pulse speed decreases as soil water content increases. If the pulse travel time is a relatively simple function of the soil real electrical permittivity, $\in_r$, then the propagation velocity, $v_p$, of the pulse is described by $$v_p = c_o(\in_r \mu)^{-0.5} \qquad [3]$$

where $c_o$ is the speed of light in a vacuum, and $\mu$ is the magnetic permeability of the dielectric material (Topp et al., 1980, Electromagnetic determination of soil water content: Measurements in coaxial transmission lines, Water Resources Research, vol. 16, no. 3, pp. 574-582). However, for a TDR probe in a soil the dielectric material between the probe rods is a complex mixture of air, water and soil particles giving rise to dielectric losses such that the apparent permittivity, $\in_a$, has both real and imaginary parts:

$$\varepsilon_a = \frac{\mu \varepsilon'}{2}\left(1 + \left\{1 + \left[\left(\varepsilon''_{relax} + \frac{\sigma_{dc}}{\omega \varepsilon_o}\right)/\varepsilon'\right]^2\right\}^{0.5}\right) \qquad [4]$$

where $\in'$ is the real component of the complex dielectric permittivity, $\in''_{relax}$ is the imaginary component of permittivity due to relaxation losses, $\sigma_{dc}/\omega$ is the imaginary component of permittivity due to conductive ($\sigma_{dc}$) and frequency ($\omega$) related dielectric losses and the other terms are previously defined. Although Eq. [4] is for a single frequency, it includes the effects that are important interferences to the EM methods. As the effective frequency decreases (e.g. due to low-pass filtering by coaxial cables, or due to the low base frequency of capacitance sensors and the declining frequency of these sensors with increasing soil water content), the value of $\sigma_{dc}/\omega$ increases, leading to larger values of $\in_a$. As conductivity increases (soils with larger BEC), the value of $\in_a$ increases, more so at lower frequencies. And, as relaxation losses increase (e.g. bound water effects), the value of $\in_a$ increases. For broad band signals such as that of TDR, the angular frequency ($\omega = 2\pi f$) may be replaced by an effective frequency, f (Robinson et al., 2003, A review of advances in dielectric and electrical conductivity measurement in soils using time domain reflectometry, Vadose Zone Journal, vol. 2, no. 4, p. 444), which previously has been calculated for TDR in at least four different ways (Schwartz et al., 2009a, Complex permittivity model for time domain reflectometry soil water content sensing. I. Theory. Soil Sci. Am. J. 73(3):886-897; Evett et al., 2005, TDR laboratory calibration in travel time, bulk electrical conductivity, and effective frequency. Vadose Zone J. 4:1020-1029; Or and Rasmussen, 1999, Effective frequency of TDR travel time-based measurement of bulk dielectric permittivity. Third Workshop on Electromagnetic Wave Interaction with Water and Moist Substances, Athens, Ga., USA, 11-13 Apr. 1999. Pp. 257-260; Topp et al., 2000, ibid).

The measured property in the TDR method is the travel time, $t_t$, of the electronic pulse (voltage step) along the length (L) of the probe rods that are exposed to the soil (FIG. 1). The velocity of the pulse can be calculated as $v_p = 2L/t_t$. Assuming $\mu = 1$, one sees that an apparent permittivity, $\in_a$, may be determined for a probe of known length, L, by measuring $t_t$ and rearranging Eq. [3], replacing $\in_r$ with the more realistic $\in_a$, to obtain $$\in_a = [c_o t_t/(2L)]^2 \qquad [5]$$

Topp et al. (1980, ibid) found that a single polynomial function described the relationship between volumetric water content, $\theta_v$, and values of $\in_a$ determined from Eq. [2] for four mineral soils.

$$\theta_v = (-530 + 292\in_a - 5.5\in_a^2 + 0.043\in_a^3)/10^4 \qquad [6]$$

Since 1980, other researchers have shown that the relationship between $\theta_v$ and $t_t/(2L)$ is practically linear (e.g., Ledieu et al., 1986, A method of measuring soil moisture by time-domain reflectometry. J. of Hydrology 88, 319-328; Yu et al., 1997, Two- and three-parameter calibrations of time domain reflectometry for soil moisture measurement. Water Resour. Res. Vol. 33. No. 10, pp. 2417-2421). Indeed, Topp and Reynolds (1998, Time domain reflectometry: A seminal technique for measuring mass and energy in soil. Soil Tillage Res. 47(1,2): 125-132) found that the polynomial calibration of Topp et al. (1980, ibid) is usefully replaced by a linear equation in travel time: $\theta_v = 0.115(c_o t_t/(2L))-0.176$. We note here that the apparent permittivity, as calculated from travel time using Eq. [5], is affected by any deviation from unity of $\mu$ because $\mu$ was considered equal to unity in the derivation of Eq. [5]. In addition, the value of $\in_a$ typically increases with the bulk electrical conductivity, $\sigma_a$ (S m$^{-1}$), of the soil, particularly for fine-textured super active soils (Wyseure et al., 1997, Measurement of volumetric water content by TDR in saline soils. Eur. J. Soil Sci. Vol. 48, pp. 347-354; Robinson et al., 2003, ibid), and particularly for $\sigma_a > 0.2$ S m$^{-1}$. Also, the value of $\sigma_a$ increases with soil water content (Rhoades et al., 1976, Effects of liquid-phase electrical conductivity, water content, and surface conductivity on bulk soil electrical conductivity. Soil Sci. Soc. Am. J. Vol. 40. pp. 651-655; Mmolawa and Or, 2000, Root zone solute dynamics under drip irrigation: A review. Plant and Soil. Vol. 222. pp. 163-190). The value of $\in_a$ may increase or decrease with temperature depending on the soil texture (Campbell, 1990, Dielectric properties and influence of conductivity in soils at one to fifty megahertz. Soil Sci. Soc. Am. J. Vol. 54, pp. 332-341; Pepin et al., 1995, Temperature-dependent measurement errors in time domain reflectometry determinations of soil water. Soil Sci. Soc. Am. J. Vol. 59, pp. 38-43; Persson and Berndtsson, 1998, Texture and electrical conductivity effects on temperature dependency in time domain reflectometry. Soil Sci. Soc. Am. J. Vol. 62, pp. 887-893; Wraith and Or, 1999, Temperature effects on soil bulk dielectric permittivity measured by time domain reflectometry: Experimental evidence and hypothesis development. Water Resour. Res. Vol. 35. No. 2, pp. 361-369), and increases as measurement frequency decreases (Campbell, 1990, ibid). The latter fact means that, for a broadband method such as TDR, there is a cable length effect because coaxial cable acts as a low pass filter—the longer the cable the less signal energy is present in the higher frequencies. The TDR estimated value of $\in_a$ increases with cable length (Hook and Livingston, 1995, Reducing propagation velocity measurement errors in time domain reflectometry determinations of soil water, Soil Sci. Soc. Am. J, vol. 59, pp. 92-96), particularly for high surface area soils (Logsdon, 2000, Effect of cable length on time domain reflectometry calibration for high surface area soils. Soil Sci. Soc. Am. J. Vol 64, pp. 54-61). Topp et al. (2000, Impacts of the real and imaginary components of relative permittivity on time domain reflectometry measurements in soils. Soil Sci. Soc. Am. J. 64:1244-1252) found that TDR signal dielectric loss is a function of $\sigma_a$, regardless of whether this conductivity arises from soil water solution conductivity or from clay type and content. Thus, TDR calibrations should take $\sigma_a$ into account, and probably cable length as well.

Although TDR is difficult to use deeply in soil profiles, the effects of bound water and $\sigma_{dc}/\omega$ for TDR are both smaller and better understood; and calibration methods exist that practically eliminate temperature and conductivity effects for TDR by taking into account the effective frequency and bulk electrical conductivity (Evett et al., 2005, ibid) and by taking into account these and the bound water content effect on $\in''_{relax}$ (Schwartz et al., 2009a, ibid; Schwartz et al., 2009b, Complex permittivity model for time domain reflectometry soil water content sensing. II. Calibration. Soil Sci. Soc. Am. J. 73(3):898-909). And with TDR, the EM field generated by the voltage pulse is forced to pass along electrodes and be affected by both drier and wetter soil peds. That this results in a true average response to permittivity variations along the electrodes has been well established (Ferré et al., 1996, Spatial averaging of water content by time domain reflectometry: Implications for twin rod probes with and without dielectric coatings, Water Resources Research, 32(2):271-279; Hook and Livingston, 1995, ibid) which fact distinguishes TDR methods from the capacitance methods, which are influenced by the small-scale spatial arrangement of variations in soil water content and $\sigma_a$. If TDR methods can be made easier to apply, more reliable and amenable to deep measurement without soil disturbance, then TDR methods may eventually supplant the neutron probe for determinations of crop water use and water use efficiency.

Methods for accurate determination of TDR pulse travel time are not trivial as has been illustrated by Evett's (2000a, The TACQ Program for Automatic Time Domain Reflectometry Measurements: I. Design and Operating Characteristics. Trans. ASAE. 43(6):1939-1946; 2000b, The TACQ Program for Automatic Time Domain Reflectometry Measurements: II. Waveform Interpretation Methods. Trans. ASAE. 43(6):1947-1956) descriptions of waveform interpretation algorithms. Although similar to TDR in attempting to determine a pulse travel time, most of the TDT methods do not accurately determine travel time due to problems with their algorithms for pulse reflection analysis (Evett et al., 2006, ibid). Most TDT methods do not acquire a waveform and so cannot apply the graphical waveform analysis described by Evett (2000a, ibid; 2000b, ibid) and used in the TACQ program copyrighted by Evett in 1992. That prevents those methods from finding the true travel time. One exception is the TDT method described by Anderson (U.S. Pat. Nos. 6,657,443, 6,831,468) in which a waveform is acquired and graphical analysis is performed.

However, despite these and other advances, the need remains for improved techniques for determining soil water content and BEC.

SUMMARY OF THE INVENTION

We have now developed an improved apparatus and method for measuring soil water content and bulk electrical conductivity (BEC) by time domain reflectometry (TDR). The apparatus allows the user to determine water content and BEC, including temperature, at multiple depths in the soil such that the entire soil profile from the surface to a user-selected depth may be characterized. The invention employs TDR, involving the injection of a short rise-time pulse into an electrode and the capture of the reflected pulse at multiple times. A waveform of reflection coefficient versus time is determined, which may be used to determine the pulse travel time and reflection coefficients at times necessary for the determination of the soil water content and BEC. The apparatus of the invention comprises:

a) a hollow, substantially cylindrical tube comprising an exterior and interior surface with upper and lower ends, said tube constructed at least in part from a non-conductive material;

b) at least two but preferably three electrodes mounted longitudinally onto said exterior surface of said tube, one of said electrodes adapted to transmit an electronic pulse therethrough and designated a voltage electrode, and the other two electrodes comprising ground electrodes;

c) an electronic pulse generator in communication with said voltage electrode effective for transmitting a short rise-time electronic pulse therethrough;

d) a voltage receiver in communication with said voltage electrode effective for receiving or capturing a reflected pulse (waveform signal) therefrom.

The apparatus may also include associated TDR and measurement electronic circuitry mounted thereon for calculating the soil water content and BEC from the measured reflected pulse.

In use, the apparatus is embedded in the soil with the electrodes in contact therewith, and in simplest terms an electronic pulse is transmitted from the electronic pulse generator through the voltage electrode, whereupon the reflected pulse from the voltage electrode is received by the voltage receiver. The pulse travel time through the voltage electrode is determined, and the soil water content may be calculated therefrom by a TDR calibration. In particular, a train of said pulses is transmitted through the voltage electrode and the reflection coefficients (reflected voltage divided by incident voltage) are captured such that a waveform of reflection coefficient values versus time is acquired from which the pulse travel time and effective frequency are determined. Also, the bulk electrical conductivity is determined from the reflection coefficient values for the incident pulse and the reflected pulse at long time. And, in a preferred embodiment the water content is calculated from a calibration based on travel time, bulk electrical conductivity and effective frequency.

In accordance with this discovery, it is an object of this invention to provide an improved TDR apparatus and method for measuring the soil water content and bulk electrical content with greater accuracy.

Another object of the invention is to provide an improved TDR apparatus and method to determine water content, BEC and temperature at multiple depths in the soil such that the entire soil profile from the surface to a user-selected depth may be characterized.

It is also an object of the invention is to provide an improved TDR apparatus having integrated electronic circuitry to form a soil water content, temperature and bulk electrical conductivity sensor that is fully functional and capable of delivering not only raw TDR waveform, reflection coefficient, waveform effective frequency and soil temperature data, but which is also capable of applying waveform interpretation and analysis algorithms internally and determining soil water content, bulk electrical conductivity and temperature data directly.

Other objects and advantages of the invention will become readily apparent from the ensuing description.

DETAILED DESCRIPTION OF THE INVENTION

The soil water content and BEC sensor system of this invention includes one or more tubes or tube segments, each having multiple three-electrode TDR waveguides (transmission lines) and associated TDR and temperature measurement electronic circuitry mounted longitudinally on individual cylindrical non-conductive tube segments that may be interconnected electrically and physically to form a hollow cylindrical down-hole soil water, temperature and bulk electrical conductivity sensor system that results in a hollow tube of user-chosen length that may be installed vertically or at any angle to vertical by augering from within. The multiple three-electrode waveguides and associated circuitry and firmware of the sensors are fully capable of measuring pulse travel time, inferring the dielectric permittivity of the soil medium, measuring the reflection coefficient values necessary for BEC determination, measuring the soil temperature, and determining soil water content based on a calibration in terms of travel time, BEC and temperature.

The electrodes are in groups of three, such that there is one center signal-carrying electrode flanked by grounded electrodes (i.e., an unbalanced single-ended transmission line). This unbalanced single-ended structure does not necessitate the use of a balun to connect to the signal generation and measurement electronics; and it allows determination of soil bulk electrical conductivity without the inaccuracies caused by a balun. The elimination of a balun also removes the singularities that restrict bandwidth and limit the resolution of the system. The downside of a single-ended system is that it is vulnerable to common mode noise, whereas a balanced differential system is not. However, with ample time available for digitizing multiple waveform readings the effects of common mode noise can be averaged out. The waveguide electrode lengths are only slightly smaller than tube segment lengths so that virtually complete characterization of the soil profile is ensured. Digital data transmission from each segment to a datalogging and wireless communication system mounted on top of the upper-most segment allows continuous data recording and wireless transmission.

Figure 2:
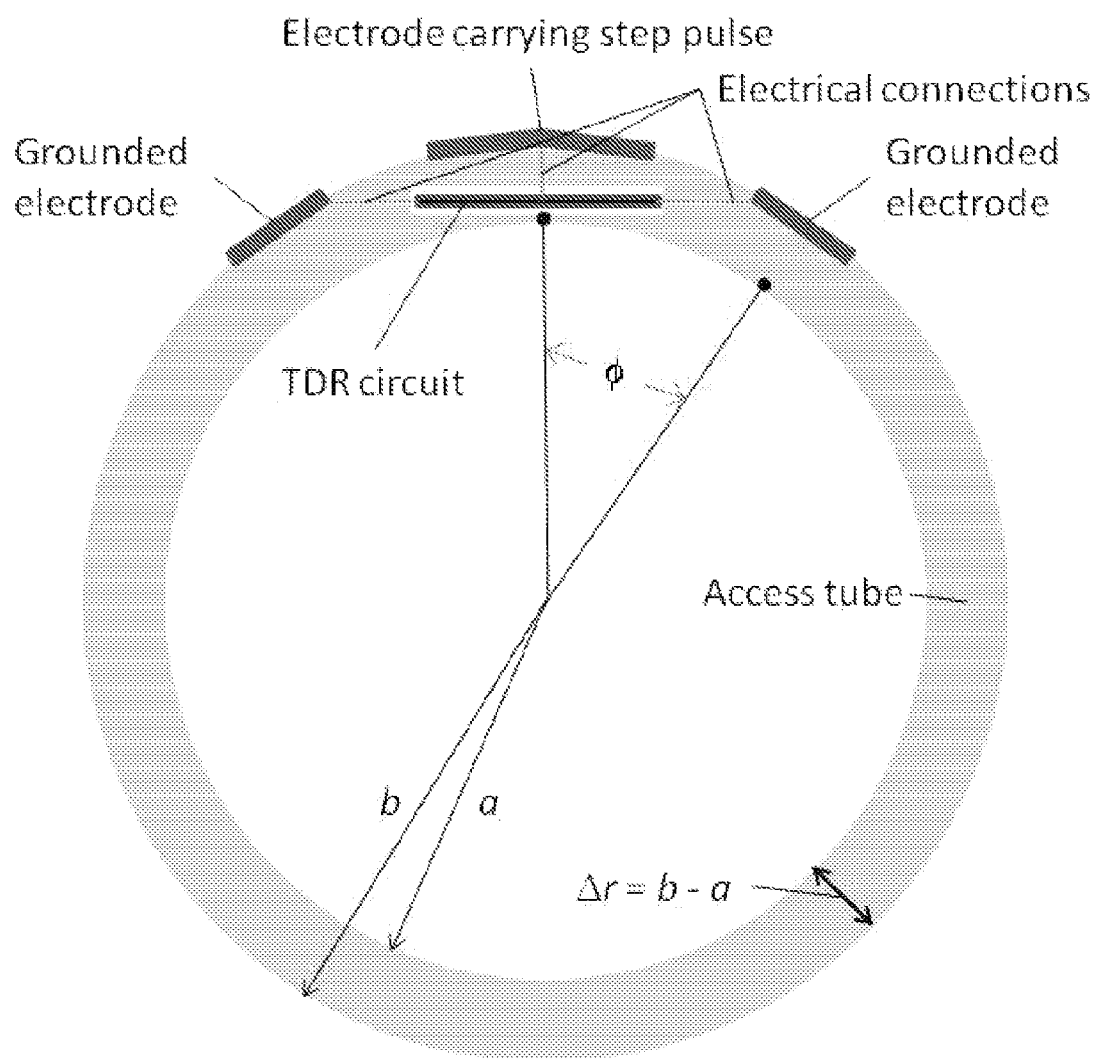
FIG. 2 shows a waveguide-on-access tube TDR sensor cross section and parameterization of the invention showing the access tube dielectric of given radial dimensions (a and b), three-electrode TDR waveguide with given angular separation ($\phi$) between the electrodes and relative position of TDR circuit within the access tube wall and connected to the electrodes.
Figure 3:
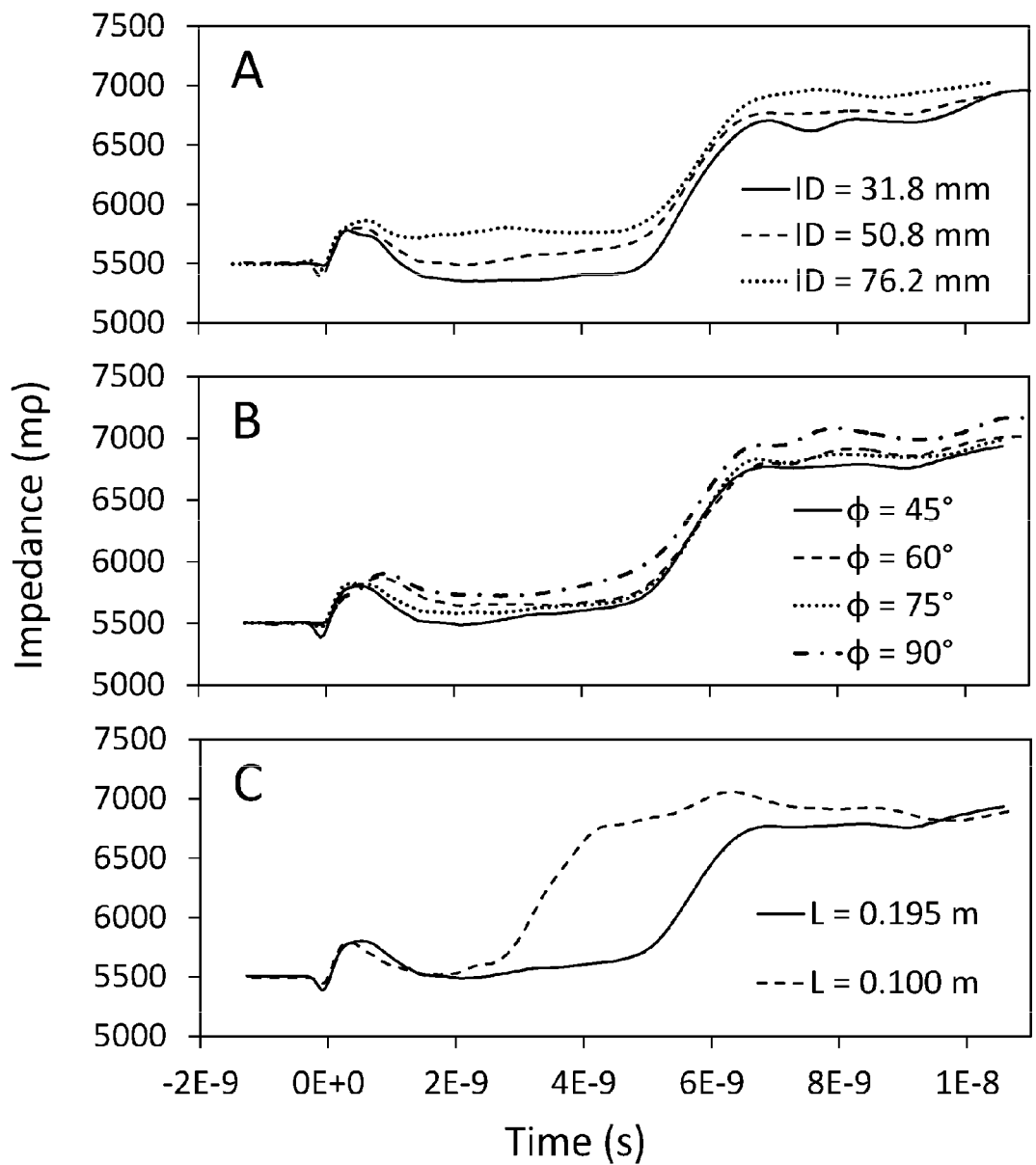
FIG. 3 shows the waveforms at saturation in sand: (a) effect of changing access tube diameter (ID is inside diameter, a), while electrode length (L) is fixed at 0.195 m and electrode separation angle ($\phi$) is fixed at 45°; (b) effect of changing $\phi$, while L is fixed at 0.195 m and ID is fixed at 50.8 mm; (c) effect of changing L, while 0 is fixed at 45 and ID is fixed at 50.8 mm.
Figure 4:
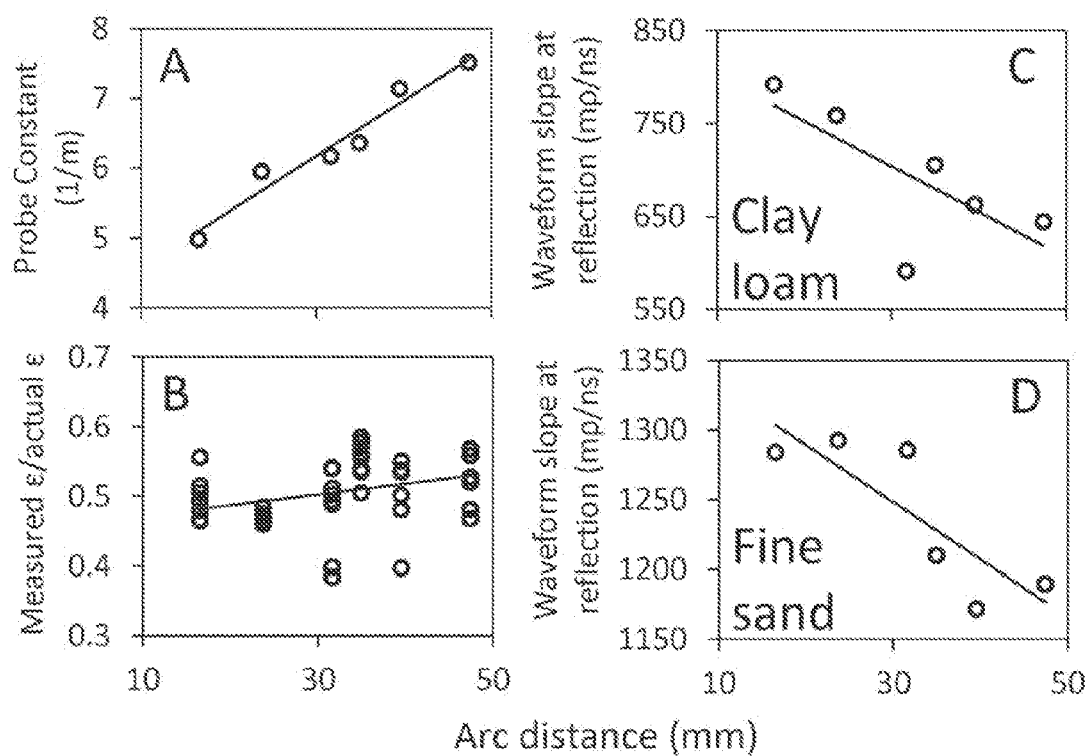
FIG. 4 shows the performance metrics versus electrode separation arc distance, with linear regressions for: (a) probe constant, (b) measured E/actual E, and waveform slope (mρ ns$^{-1}$) at second reflection in (c) clay loam and (d) in fine sand.
Figure 5:
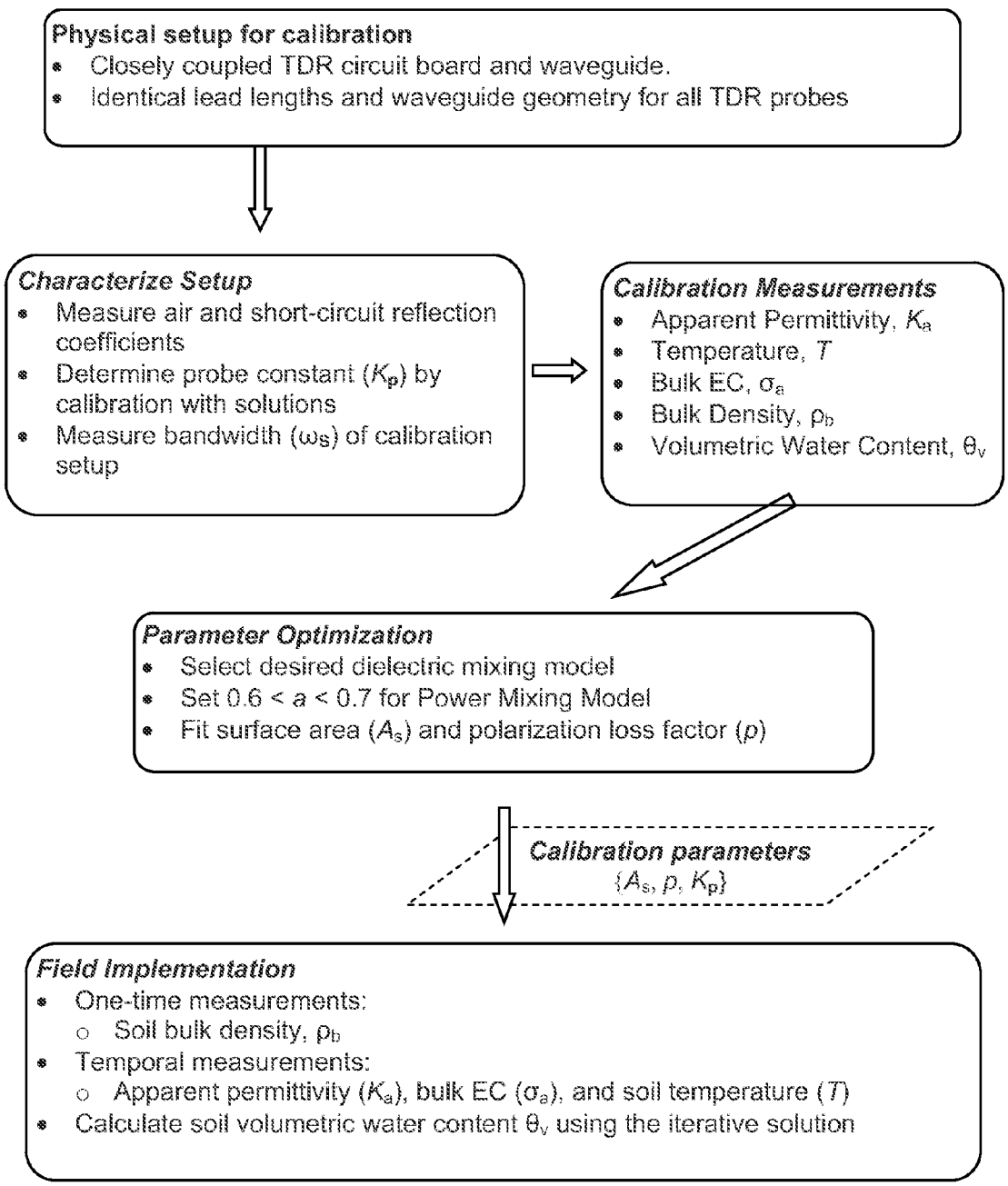
FIG. 5 shows a flow chart detailing the generalized calibration procedure and field implementation of the complex permittivity model for soil water content sensing in accordance with this invention (second alternative calibration described below).

As shown in FIG. 2, the spacing of electrodes on the tube may be characterized by angular separation or arc-wise distance of separation (FIG. 2). A variety of suitable angles may be chosen (e.g., 45, 60, 75 and 90 degrees), but larger angles decrease sensitivity to soil bulk EC changes and smaller angles increase electrical losses due to bulk EC and may also decrease EM field penetration into the soil thus reducing sensitivity to soil dielectric permittivity (FIG. 3). Larger arc distances (angles) increase the probe constant used in calculation of bulk EC from reflection coefficient values (FIG. 4). Increasing arc distance decreases the waveform slope at the second reflection, which decreases the accuracy of travel time (and thus water content) determination (FIG. 4). Arc distance has little effect on estimated apparent permittivity, but the tubing dielectric properties and air-filled space within the tube cause the estimated apparent permittivity to be less than the measured soil permittivity because the EM field is affected by the air and tubing dielectric values, which are 1 for air and may be approximately 5 for the tubing (FIG. 4).

The thickness ($\Delta r = b-a$) of the tube dielectric material may vary as may the radius (a) of the inside and the radius (b) of the outside surfaces of the tube (FIG. 2). For a given angular separation, increasing the outer surface radius (b) increases the arc distance between electrodes, which decreases sensitivity to soil BEC and may promote EM field penetration into the soil (FIG. 3). Although the tubing dielectric material is typically plastic, the exact material may vary.

A short rise time step function generator and waveform digitizer are also mounted immediately at the transmission line (waveguide) origin such that the full TDR function is closely integrated into a self-contained fully functional TDR sensor. This architecture preserves bandwidth for high resolution waveform analysis and is inherently much lower in cost than conventional, lower bandwidth TDR systems with voltage step pulse rise times in the 120 to 200 ps range. Conventional TDR systems consist of a metallic time domain reflectometer (TDR) instrument connected by coaxial cable to one or more coaxial multiplexers (e.g., Evett, 1998), which are themselves connected and interconnected by coaxial cable to one or more TDR probes, which themselves are waveguides containing no active parts being only two, three or more metallic (usually stainless steel) electrodes connected to the coaxial cable in a probe head such that one of the electrodes is connected to the center conductor of the coaxial cable and the others are connected to the outer braid (virtual ground) of the coaxial cable and act as the ground rods of the waveguide system, the center-connected electrode being the one carrying the step pulse. The TDR instrument and multiplexers are controlled by a computer/microcontroller, either situated inside the instrument or externally connected to it and in any case connected to the multiplexers as well, typically using digital logic (for example, using standard PC serial and parallel ports). The ensemble is a supervisory control and data acquisition system such as that described by Evett (1994, TDR-Temperature arrays for analysis of field soil thermal properties. Pp. 320-327 In Proc. Symp. on TDR in Environment Infrastructure and Mining Application, Northwestern Univ., Evanston, Ill.). The computer/microcontroller interprets the waveforms and in some cases also calculates soil bulk electrical conductivity from reflection coefficient data and knowledge of the coaxial cable lengths and associated probe constants (e.g., Evett et al., 2005, ibid). By contrast, our invention integrates the TDR instrument and temperature sensor with the waveguide to form a soil water content, temperature and bulk electrical conductivity sensor that is fully functional and capable of delivering raw TDR waveform, reflection coefficient, waveform effective frequency and soil temperature data for interpretation elsewhere and also is capable of applying waveform interpretation and analysis algorithms internally and delivering soil water content, bulk electrical conductivity and temperature data directly. In the preferred embodiment of the invention, which involves close coupling of the TDR circuit to the electrodes, the apparatus of this invention avoids electrical losses due to low-pass filtering of the high frequency components of the voltage pulse by the coaxial cabling, connections and multiplexers of conventional systems and thus avoids inaccuracies due to different frequency spectra for probes at different cable lengths from the TDR instrument. It avoids the cabling (length and loss characteristics), connection and multiplexer effects on the reflection coefficients needed for computation of the bulk electrical conductivity To facilitate the placement of the sensor in the soil, the apparatus preferably includes an auger disposed within the tube sub-system said tube having a beveled cutting edge at its forward edge allowing installation of the tube with intimate contact to undisturbed soil along the outside of the tube. Also provided for are sealing of the tube at the bottom and top ends.

The electromagnetic design system described above optimizes waveguide electrode size and angular spacing as well as thickness, diameter, and dielectric constant of the tube segment cylinder material to guarantee maximal EM field penetration into the soil medium and minimal losses.

In use, the calibration system for soil water content is in terms of pulse travel time, soil BEC, soil temperature, and incorporates influences of the geometry and dielectric properties of the waveguide-on-tube system on measured pulse travel time, such that bound water effects on the soil apparent dielectric permittivity are quantified and temperature effects on water content values are minimized. The pulse travel time is determined using waveform interpretation algorithms described by Evett (2000a, ibid, and 2000b, ibid, the contents of each of which are incorporated by reference herein) and new algorithms described here. Two calibration systems may be used, with the choice between them depending on ancillary data that may be available to the user (principally the soil texture and particle surface area). The first, and simpler, calibration system uses the calibration of Evett et al. (2005, ibid) where volumetric soil water content ($\theta_w$) is related to the travel time, the effective frequency ($f_{vi}$) of the voltage pulse and $\sigma_a$ according to $$\theta_v = a + b[c_a t_i/(2L)] + c[\sigma_a/(2\pi f_{vi} \epsilon_o)]^{0.5} \qquad [7]$$

where a, b, and c are calibration coefficients, L is the sensor electrode length. The value of the effective frequency is determined by the highest slope, $\Delta V_f$, of the second rising limb of the waveform (after $V_{min}$ in FIG. 1), which represents the reflection of the TDR pulse at the end of the probe rods, and from the magnitude of the initial voltage step (TDR pulse height), which is $V_{02} - V_i$. The TACQ program was modified to output the slope value and the time base, $t_b$ (ns per unit) of the waveform; and the magnitude of the initial voltage step was calculated as $V_{02} - V_i$ from the reflection coefficient data related to $\sigma_a$ output by TACQ. This differs from the procedure used by Topp et al. (2000, ibid), which relied on finding the maximum value of the second rising limb in order to fit a horizontal line tangent to it. Finding this maximum value may be difficult due to multiple reflections in the waveform. Also, this maximum value decreases as $\sigma_a$ increases, leading to a reduction in the reflected pulse magnitude. The resulting reduced rise time causes the effective frequency determined by the method of Topp et al. (2000, ibid) to be larger than that determined by our method, in effect confounding the effects of $\sigma_a$ and bound water on effective frequency (slope of the reflection) with the effect that $\sigma_a$ has on the magnitude of the reflected pulse (a conduction effect).

The effective frequency (radians), with subscript vi to indicate that it is relative to the initial voltage step, is $$f_{vi} = 2\pi \times 10^9 \times \Delta V_f / [t_b (V_{02} - V_i)] \qquad [8]$$

This calibration reduces the effect of soil temperature changes on calculated water contents because it corrects for the effects of conductive ($\sigma_{dc}$) and frequency (w) related dielectric losses on apparent permittivity as indicated in Eq. [4]. Note that all the data needed for this calibration are available from the TDR waveforms acquired by our TDR circuit.

The second alternative calibration is based on that demonstrated by Schwartz et al. (2009a, ibid; 20009b, ibid). The calibration and its use to calculate water content values includes the following steps:

1. Equipment: The TDR circuit board is closely coupled to the waveguide as shown in FIG. 2, eliminating cable effects. Therefore the characteristic impedance is the output impedance of the TDR circuit board. In addition, the incident bandwidth of the TDR signal $\omega_s$ is constant. All TDR probe waveguides and connections to the circuit board are assumed to be geometrically identical.
2. Determine the final (long-time) reflection coefficient of the probe in air and short-circuited to calculate the scaled reflection coefficients (Lin et al., 2008, Clarification and Calibration of Reflection Coefficient for Electrical Conductivity Measurement by Time Domain Reflectometry, Soil Science Society of America Journal, vol. 72, no. 4, pp. 1033-1040).
3. Determine the probe constant $K_p$ with an EC calibration using a range of KCl solutions and the long-time scaled reflection coefficients (Schwartz et al., 2009b, ibid).

Once determined, this value is constant for all probes of a common geometrical configuration and can be calculated for probes of other geometrical configurations from the electrode radius and spacing as described below.
4. Prepare soil columns over a range of water contents (from air dry to near saturation) by packing soil mixed with water to a desired bulk density and volumetric water content. Near saturated columns may be prepared by packing air dry soil, wetting column from bottom, and permitting the column to drain under a slight tension approximately equivalent to column length.
5. Record travel time measurements and final (long-time) reflection coefficients of packed columns equilibrated at three temperatures (>4° C.). The temperatures should encompass the range expected in the field and should span at least 30° C. to permit a measurable change in bound water.
6. For each representative soil horizon, fit the square root of measured apparent permittivities to the square root of predicted apparent permittivities estimated from measurements of (a) soil water content, (b) temperature, (c) $\sigma_a$, (d) bulk density, and (e) bandwidth $\omega_s$. The minimization problem results in a best-fit soil-specific surface area $A_s$ and polarization loss factor p. Predicted apparent permittivities are calculated as $$K_a(\omega_R, T) = \frac{\text{Re}(\varepsilon^*(\omega_R, T))}{2} \cdot \left(1 + \sqrt{\left(\frac{-\text{Im}(\varepsilon^*(\omega_R, T))}{\text{Re}(\varepsilon^*(\omega_R, T))}\right)^2 + 1}\right) \quad [9]$$

Where $\varepsilon^*(\omega_R, T)$ is the frequency and temperature dependent complex dielectric permittivity of the soil that can be described using a power law mixing model (e.g., Birchak et al., 1974, High dielectric constant microwave probe for sensing soil moisture. Proc. IEEE 62:93-98; Dobson et al., 1984, Microwave dielectric behavior of wet soil. II. Dielectric mixing models. IEEE Trans. Geosci. Remote Sens., GE-23, 35-46; Dirksen and Dasberg, 1993, Improved calibration of time domain reflectometry soil water content measurements. Soil Sci. Soc. Am. J. Vol. 57, pp. 660-667) in combination with an imaginary conductive loss component to yield equation [10] as follows:

$$\varepsilon^*(\omega_R, T) = \left[\left(1 - \frac{\rho_b}{\rho_s} - \theta\right) \cdot (\varepsilon_a)^a + \frac{\rho_b}{\rho_s} \cdot (\varepsilon_s)^a + (\theta - \theta_{bw}) \cdot [\varepsilon_{fw}^*(\omega_R, T)]^a + \theta_{bw} \cdot [\varepsilon_{bw}^*(\omega_R, T)]^a\right]^{\frac{1}{a}} - j\frac{\sigma_a}{\omega_R \varepsilon_0}$$

where $\omega_R$ is effective angular frequency (rad s$^{-1}$), T is soil temperature, $\sigma_0$ is equivalent to $\sigma_a$ (S m$^{-1}$), $\varepsilon_a$ is gas phase permittivity, $\varepsilon_s$ is solid phase permittivity (both $\varepsilon_a$ and $\varepsilon_s$ are known), $\varepsilon_{fw}^*(\omega_R,T)$ is bulk (free) water complex permittivity, $\delta_{bw}^*(\omega_R,T)$ is bound water complex permittivity, $\rho_b$ is the soil bulk density (kg m$^{-3}$), $\rho_s$ is particle density (kg m$^{-3}$), $\theta$ is volumetric soil water content (m$^3$ m$^{-3}$), $\theta_{bw}$ is the volume fraction of bound water (m$^3$ m$^{-3}$) which is a function of specific surface area $A_s$ (m$^2$ kg$^{-1}$), a is a fitted empirical exponent (0.55<a<0.70), and $\varepsilon_0$ is the permittivity of free space (8.854×10$^{-12}$ F m$^{-1}$), and j=

$\sqrt{-1}$. This method will also accommodate other four-component mixing models described in the literature (e.g. Sihvola, 2000, Mixing rules with complex dielectric coefficients. Subsurface Sensing Technologies and Applications. 1(4):393-415, 2000; Schwartz et al., 2009a, ibid) to describe the complex permittivity of soil. Bulk water complex permittivity is described by the single Debye relaxation equation with the empirical expressions of Stogryn (1995, The microwave permittivity of sea and fresh water. Gen Corp Aerojet: Azusa, Calif.) to evaluate the temperature dependent static dielectric constant and time constant. The complex permittivity of bound water is calculated based on the equations developed by Schwartz et al. (2009a, ibid, the contents of which are incorporated by reference herein). Effective frequency, $\omega_R$, is approximated by calculating the effect of bulk and bound water polarization processes on the incident bandwidth using a fitted polarization loss factor p (Schwartz et al., 2009a, ibid). Because bulk and bound water polarization are frequency dependent, this results in an iterative problem that is solved using a root finding algorithm.

The calculation of field water contents using the second alternative calibration may be determined as follows:
1. Measure or approximate the bulk density of the soil for each depth at which TDR soil water contents are measured.
2. Record travel time and final (long-time) reflection coefficients and the corresponding soil temperature using sensors coupled to each set of waveguides; and, using the probe constant $K_p$, calculate $\sigma_a$.
3. Using the fitted surface area $A_s$ and polarization loss factor p in conjunction with parameters measured above, calculate the apparent permittivity in Eq. (9) for a selected trial water content. Because water contents must be estimated from measured values of apparent permittivity, the calculation of water content is transformed into a one-dimensional root finding problem for the function $f(\theta)$ defined as $$f(\theta) = K_a - \hat{K}_a(\theta, T, \sigma_0, \rho_b, \omega_S) \quad [11]$$

where $K_a$ is the permittivity based on travel time measurements and $\hat{K}_a$ is the predicted permittivity in Eq. [9].

Iterative bisection is used to solve the root finding problem with $\theta$ bracketed between 0 and 0.6 m$^3$ m$^{-3}$.

The measured permittivity by TDR in the waveguide-on-access-tube implementation is actually an effective permittivity which is an average of the permittivities of the waveguide substrate (tube), air, and the medium (soil) surrounding the probe. This can be accounted for by using a power-law mixing model. Using measurement of various probe geometries in various triethylene glycol mixtures, a power-law mixing model was formulated and fit. It is contained in the following set of equations:

$$\varepsilon_{\mathit{eff}}^n = \frac{A_{soil}}{A_{tot}}\varepsilon_{soil}^n + \frac{A_{pvc}}{A_{tot}}\varepsilon_{pvc}^n + \frac{A_{air}}{A_{tot}}\varepsilon_{air}^n$$

$$A_{tot} = A_{soil} + A_{pvc} + A_{air}$$

$$A_{air} = \pi ID^2$$

$$A_{pvc} = \pi OD^2 - \pi ID^2$$

$$A_{soil} = \pi c^2 OD^2 - \pi OD^2$$

where $\varepsilon_{\mathit{eff}}$ is the effective permittivity; $\varepsilon_{soil}$ is the soil permittivity; $\varepsilon_{pvc}$ is the effective substrate permittivity (assumed to be 3); $\varepsilon_{air}$ is the permittivity of air (assumed to be 1); c, n are fitted parameters; c relates the outside diameter of the pipe to the sampling volume and n is the mixing exponent; ID is the inside diameter of the PVC; and OD is the outside diameter. Using data from the triethylene glycol tests, the best fit values for c and n were 0.8292 and 1.5538, respectively.

The calibration system for $\sigma_a$ in terms of reflection coefficient values and dielectric characteristics of the waveguide-on-tube system such that $\sigma_a$ is accurately determined even though the waveguide electrodes are partially enclosed by the non-conductive tube segment cylinder of a known electrical conductivity and permittivity. Several methods are useful for $\sigma_a$ calculations (e.g., Wraith, 2002, Time domain reflectometry. Section 6.1.4.4. In J. H. Dane and G. C. Topp (eds.) Methods of Soil Analysis, Part 4, Physical Methods. Pp. 1289-1296; Castiglione and Shouse, 2003, The effect of ohmic cable losses on time-domain reflectometry measurements of electrical conductivity. Soil Sci. Soc. Am. J. 67:414-424; Lin et al., 2008, ibid), but the method of Lin et al. (2008, ibid) is preferred.

The probe is calibrated at a temperature of 22° C. in deionized water and four reference KCl solutions (2.5, 5.0, 7.5, and 10.0 mM equivalent to 0.035, 0.070, 0.106, and 0.141 S m$^{-1}$, respectively, at 25° C.). Electrical conductivity of the solutions is measured independently with a standard EC meter calibrated using the same KCl solutions. The probe constant is determined by finding the slope of the scaled reflection coefficient (Castiglione and Shouse, 2003, ibid) versus measured conductivity and multiplying by the TDR circuit board characteristic output impedance.

The bulk EC, $\sigma_a$, is calculated using $$\sigma_a = \frac{K_p}{Z_u} \frac{1 - \rho_{\infty,scale}}{1 + \rho_{\infty,scale}} \quad [12]$$

where $Z_u$ is the characteristic output impedance of the TDR circuit board and the scaled reflection coefficient ($\rho_{\infty,scale}$) is $$\rho_{\infty,scale} = 2 \frac{(\rho_{\infty,air} - \rho_{\infty,sc})(\rho - \rho_{\infty,air})}{(1 + \rho_{\infty,sc})(\rho - \rho_{\infty,air}) + (\rho_{\infty,air} - \rho_{\infty,sc})(1 + \rho_{\infty,air})} + 1 \quad [13]$$

where $\rho_{\infty,air}$ is the reflection coefficient measured with the probe in air, and $\rho_{\infty,sc}$ is the reflection coefficient with the probe shorted.

The following examples are intended only to further illustrate the invention and are not intended to limit the scope of the invention which is defined by the claims.

Example 1

This example utilizes the sensor including a cylindrical access tube with surface-mounted electrodes of this invention for use in TDR. This cylindrical geometry facilitates sensor installation at multiple depths in the soil profile. Variations in the tube and electrode geometries are tested in different media, including air, triethylene glycol, deionized water, sand, and clay loam. First, the sensor geometry is detailed; then, the construction procedure is described; finally, the results of sensor waveforms and dielectric measurements are compared across sensors and across media to assess sensor performance.

Access Tube Design and Geometrical Parameterization

FIG. 2 shows a cross-section of the probe design with design parameters. The waveguide-on-access-tube TDR design comprises a cylindrical dielectric tube, with three electrodes on its surface that may or may not be connected to voltage ground or a source voltage. The probe can be fully described by the following variables: Probe length, dielectric tube inner radius a, dielectric thickness $\Delta r$ (or outer radius b), dielectric value $\varepsilon$, electrode width and electrode spacing (or positions $\phi$). For the sake of brevity, we only consider an annulus with an air core; we don't discuss the possible case of a metal layer on the interior of the dielectric tube, although this is another option in the design. We also do not describe the case where multiple sets of waveguides are mounted on the tube although this is a likely embodiment.

Sensor Construction

The sensor prototypes were constructed from schedule 40 rigid polyvinyl chloride (PVC) tubing of various diameters, although it is stipulated that PVC is a relatively poor material in terms of dielectric losses for this purpose. The electrodes were 4.76-mm diameter stainless steel rods. To attach the electrodes to the tube body, grooves were milled. Then, the electrodes were electrically connected to a 2-m length of 50-ohm coaxial cable (LMR 240, Times Microwave Systems, Wallingford, Conn.)1. Electrical properties of the cable are given in Table I. The electrodes were affixed using room temperature vulcanizing silicone sealant and the electrical connection between the coax and the electrodes was sealed in silicone. The specific sensor prototypes that were constructed are listed in Table II.

Sensor Tests

Seven sensors were tested in different media by waveform acquisition using a Tektronix 1502B cable tester and a microcomputer running the TACQ software (Evett, 2000a, ibid). Waveforms were acquired using two time windows, one using a lower resolution of 251 points in 35 ns (7.17 points/ns) and another using a higher resolution of 251 points in 6 ns (35.86 points/ns). The tests were conducted in four main groups. First, four waveforms of 251 points were acquired and averaged in standard media: air, triethylene glycol (at various degrees of dilution with deionized water), and deionized water; then, in sand or clay loam, mixed to achieve homogeneous moisture distribution, up to 0.20 m$^3$ m$^{-3}$ volumetric water content, in increments of roughly 0.05 m$^3$ m$^{-3}$. The permittivity of the standard media was taken as the reading supplied by a standard trifilar (three-electrode) probe. Soil properties are given in Table III, where surface areas were obtained by equilibrating moistened soils at 54.4% relative humidity (Schwartz et al., 2009b, ibid) and bulk densities were the averages of packed values. Soil was contained in a 0.203-m diameter, 0.216-m high PVC cylinder. Third, sensors were evaluated in sand or clay loam at or near saturation, achieved through introducing deionized water at the bottom of the packed column at a small positive pressure head while connected to a load cell. Finally, sensor probe constants for bulk electrical conductivity calculations were determined by acquiring waveforms in KCl solutions of measured conductivity, using the relationship between reflection coefficient and conductivity described in Lin (2008, ibid).

Figure 1:
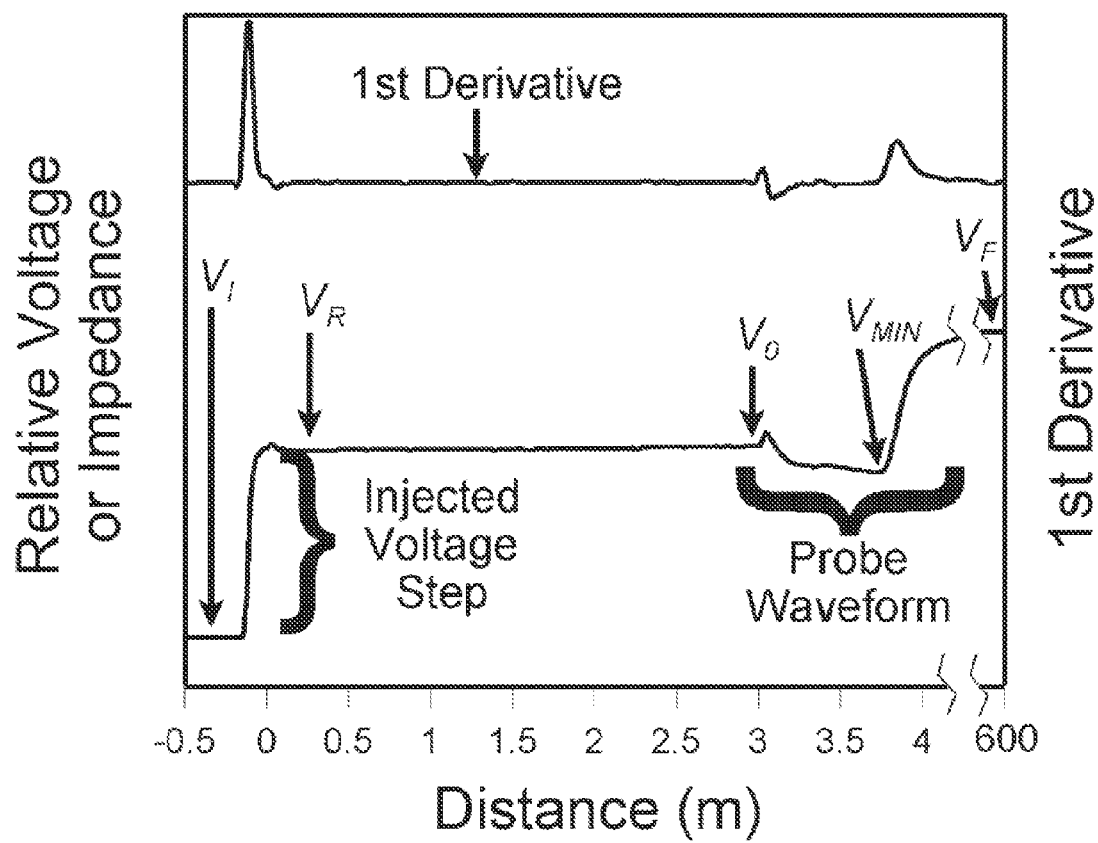
FIG. 1 shows a plot of time domain reflectometer (TDR) waveform and first derivative as seen on a TDR waveform analysis computer program. The relative voltages are: $V_I$, the initial value; $V_R$, the value after the electrical pulse is injected inside the metallic time domain reflectometer; $V_O$, the value in the coaxial cable just before the TDR probe; $V_{MIN}$, the value at the lowest point in the part of the waveform that corresponds to the TDR probe; and $V_F$, the final value at maximum distance (approximately 600 m). The X-axis is shown as distance, but the base measurement is time (t) and distance (L) is derived from the relationship $L=v_p t$, where $v_p$ is the propagation velocity of the pulse within the coaxial cable or waveguide (probe). The propagation velocity is well characterized for coaxial cables for which it changes according to cable construction, but is inherently unknown for soils, where it depends on soil properties, principally the water content.

In discussion of TDR waveforms here we will use the waveform nomenclature of Schwartz et al. (2009a, ibid; 2009b, ibid) and Evett et al. (2005, ibid), which relates to measurements of pulse travel time, final reflection coefficient (relative impedance) and slope of the waveform reflection at the electrode ends defined there and in Schwartz et al. (2009a, ibid; 2009b, ibid). A labeled waveform and its derivative are shown in FIG. 1.

To evaluate sensor performance in soil, several metrics were employed. Waveforms were compared across sensors and media. Differences in probe response with respect to water content in sand and clay loam media were assessed using general linear models in SAS with a quadratic model and probe design as a classification variable (excluding the short, 10 cm, probe, whose travel times are necessarily shorter than the other, longer probes). The quadratic model was ultimately chosen because the quadratic term was significant. In the air, triethylene glycol, and deionized water tests, the TDR-estimated apparent permittivity was compared to the apparent permittivity as measured by a standard trifilar probe to give an indication of the probe's field penetration into the surrounding media. In the soils, the data were analyzed by comparing waveform slope at the second reflection. This gives a measure of waveform quality; higher slope indicates a less degraded waveform as the high frequency components of the input pulse are not attenuated as strongly.

Figure 6:
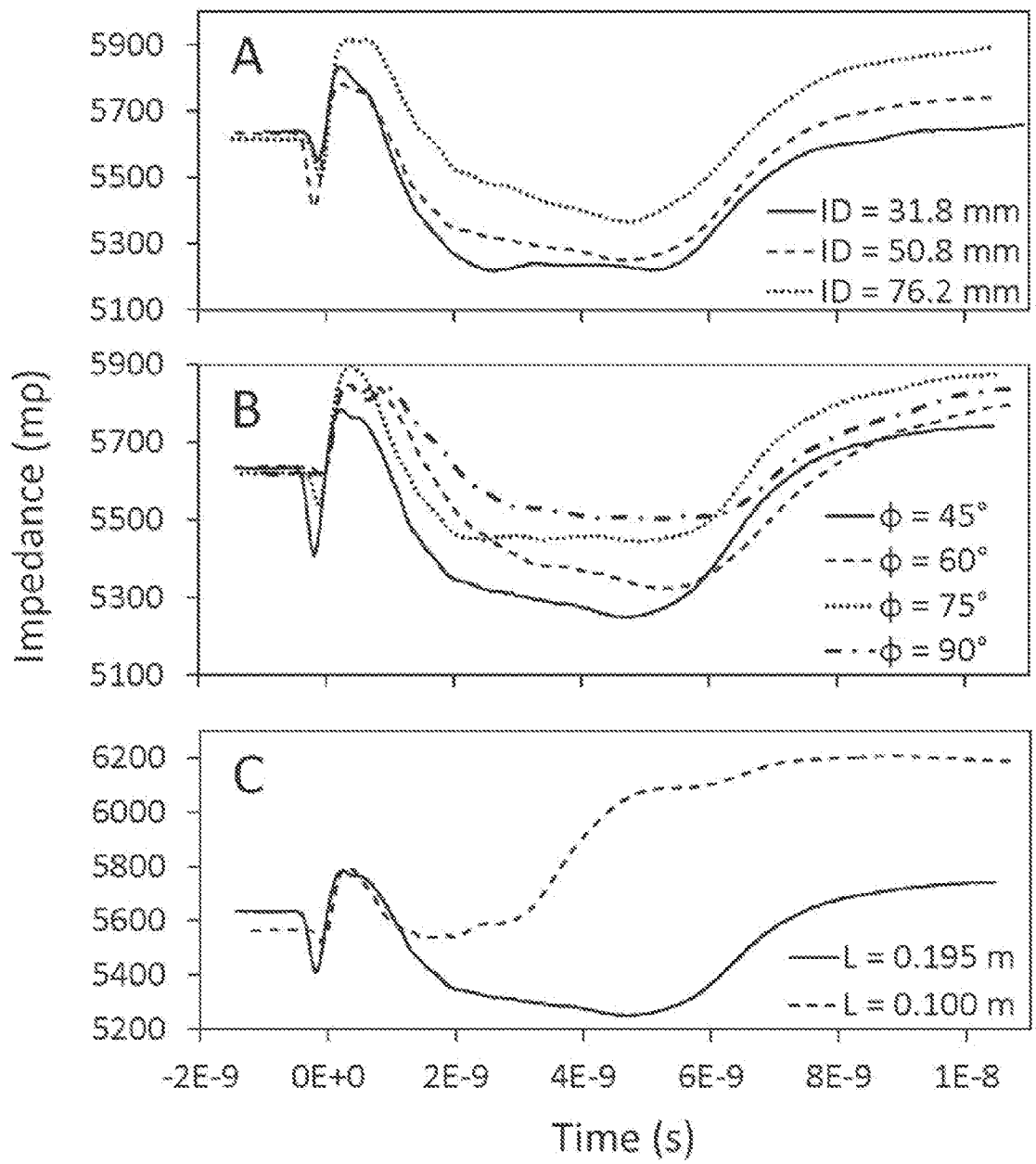
FIG. 6 shows the waveforms at saturation, for all sensors, in clay: (a) effect of changing ID, while L is fixed at 0.195 m and f is fixed at 45; (b) effect of changing f, while L is fixed at 0.195 m and ID is fixed at 50.8 mm; (c) effect of changing L, while f is fixed at 45 and ID is fixed at 50.8 mm, as described in Example 1.
Figure 7:
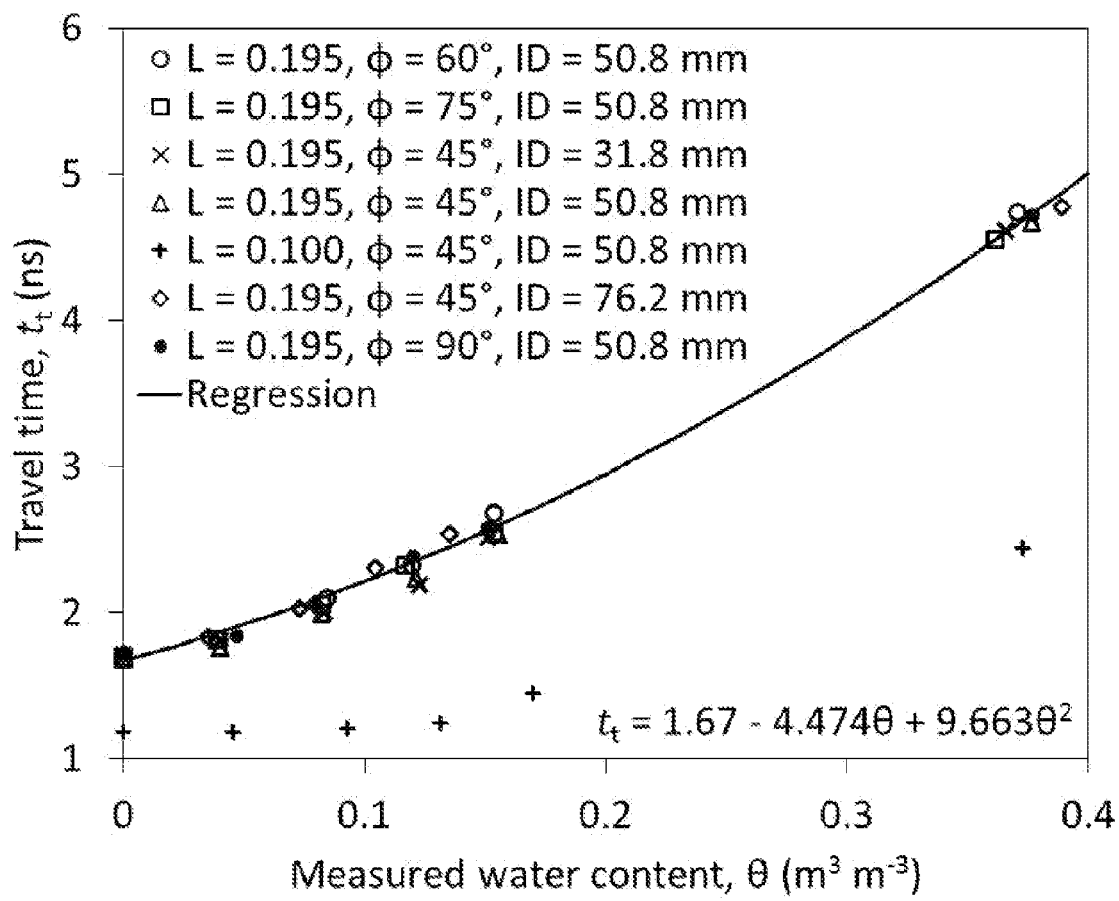
FIG. 7 shows the effects of actual volumetric soil water content (VSW) on travel time, with quadratic regression, in sand, as described in Example 1.

Acquired waveforms in sand and clay loam media varied among sensor designs principally at or near saturation as a result of greater signal degradation at higher water contents. Comparison of waveforms from different diameter sensors in near-saturated (0.38 m$^3$ m$^{-3}$) sand shows that the waveform depression after the initial peak and before the final reflection (end of electrodes) increases as diameter decreases (FIG. 3($a$)), indicating a lower characteristic impedance. This is in part due to the decreasing physical electrode separation as diameter decreases for the constant angular electrode separation. This result is corroborated by the fact that for a constant diameter, decreasing angular separation also caused the waveform depression to mostly increase between initial peak and final reflection (FIG. 3($b$)). The effect of electrode length on travel time is as expected (FIG. 3($c$)). Waveforms in near-saturated clay loam show more obvious inter-sensor differences (FIG. 6), as the water content is higher (0.48 m$^3$ m$^{-3}$) and clay loam has more high-frequency losses.

Figure 8:
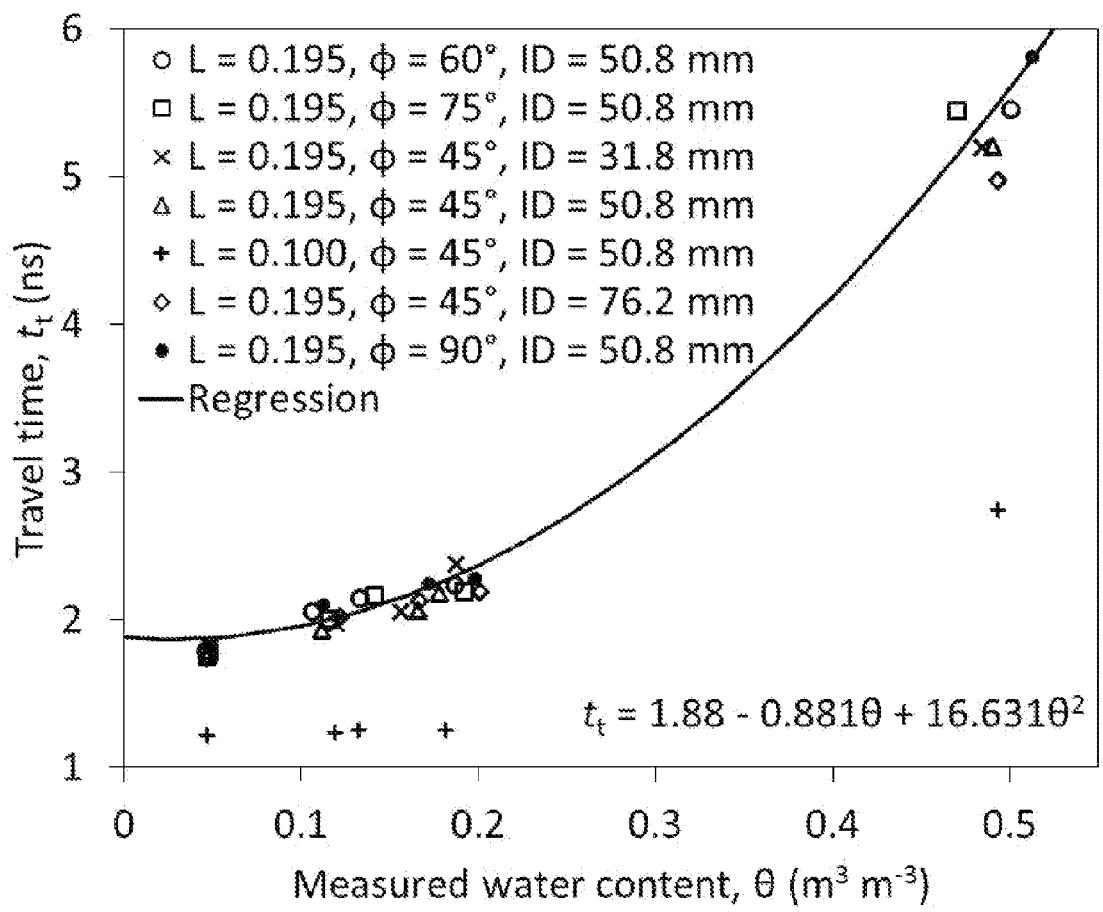
FIG. 8 shows the effects of actual volumetric soil water content (VSW) on travel time, with quadratic regression, in clay, as described in Example 1.

In sand, the waveform differences among sensors are fairly indistinct (aside from the effect of electrode length shown by the 0.10 m probe), and consistent with a nonsignificant (P=0.38) probe design effect on the quadratic response of travel time with respect to volumetric water content. Although a linear response between travel time and water content is theoretically predicted for sand, modeled linear and quadratic responses were highly significant (P<0.001). This result is evidently a result of the contributions of the PVC fraction to the permittivity and its dependency on water content. Modeled response of travel time to water content in the clay loam soil (FIG. 8) also had a significant quadratic response (P<0.001), however the linear term was nonsignificant (P=0.511).

Comparing the TDR-estimated apparent permittivity (E) to the known permittivity of fluids gives a measure of the field penetration into the media. Since the surrounding permittivity is different than the permittivity of the PVC (about 3) and air core (about 1), a greater penetration of the electromagnetic field into the surrounding media would be manifested by a measured permittivity closer to the known value. Consequently, the ratio of measured permittivity to known permittivity would approach unity as the field penetration increases. The relationship between this ratio and electrode separation was examined by a linear regression (shown in FIG. 4($b$)), using the data from the triethylene glycol and deionized water tests. The slope of this regression was statistically significant (P=0.0195) and positive, showing that field penetration increases with increasing electrode separation. However, the RMSE of regression was +/−0.045, the same order of magnitude as the change in measured ∈/actual ∈ over the range of arc distances, indicating that a strong relationship is not clear.

The mean maximum slope of the waveform at the open termination reflection (FIG. 1; to the right of V$_{min}$) in sand and in clay loam were compared across sensors and with respect to arc distance between electrodes. For a given bulk EC, a lower slope is indicative of a narrower bandwidth resulting from signal attenuation at higher frequencies (Topp et al., 2000, ibid). In sand, the slopes were greater than in the clay loam, as sandy soils have less high-frequency dielectric losses (Schwartz et al., 2009b, ibid) [16]. In both sand and clay loam, the slope of the reflection decreased with increasing arc separation distance (FIGS. 4($c$ and $d$)) despite the fact that greater separation distances are associated with a larger probe constant and less attenuation of long-time reflection coefficients. Such a result is indicative of greater signal attenuation at high frequencies caused by dielectric relaxation mechanisms and associated with a greater field penetration into the soil for probes with greater electrode separation distance.

Calibrated probe constants ranged from 5 to 10 m$^{-1}$ and were considerably greater than constants of standard TDR probes of similar lengths. A lower probe constant indicates the probe has a greater sensitivity to DC soil conductivity. The most sensitive probe was the 31.8-mm diameter probe, followed by the 50.8-mm diameter sensors, in order from 45-degree separation to 90-degree separation. Sensitivity to conductivity increased with decreasing electrode separation (FIG. 4$a$)), and correlated closely (r=0.988) with an analytical derivation of three-electrode probe constants by Paolo Castiglione (personal communication. 2008). We have surprisingly discovered that the probe constant for our three-electrode waveguide on access tube design can be predicted for any combination of electrode length (L), electrode radius (r$_L$) and electrode arc-wise spacing (s) by a simple quadratic function of the probe constant (K$_{p\_c}$) estimated by the equation of Castiglione which is $$K_{p\_c} = \frac{1}{4\pi L} \ln\left(\frac{1-d^4}{2d^3}\right) \quad [18]$$

where d=r$_L$/s. The quadratic function to determine the probe constant for the waveguide on access tube configuration is $$K_p = -0.202 K_{p\_c}^2 + 3.175 K_{p\_c} - 2.124 \quad [19]$$

The probe constant is related to the electrode separation, which conforms to the predictions of a TEM field model, but only at DC. Increasing field penetration (as measured by slope at reflection and the permittivity ratio discussed earlier) with increasing electrode separation match the prediction of the hybrid mode propagation derived in (Casanova et al., 2011. Design of access-tube TDR sensor for soil water content: Theory. IEEE Sensors J., PP(99):1-1. DOI:10.1109/JSEN.2011.2181354).

It is understood that the foregoing detailed description is given merely by way of illustration and that modifications and variations may be made therein without departing from the spirit and scope of the invention.

TABLE I

LMR-240 PROPERTIES.

| | |
|---|---|
| Cutoff frequency | 31 GHz |
| Velocity of Propagation | 84% |
| Impedance | 50 |
| Attenuation at 2 GHz | 37.7 dB/100 m |

TABLE II

SENSOR PROTOTYPE DIMENSIONS.

| Probe number | ID (mm) | OD (mm) | f (deg) | Arc distance (center to ground, mm) | L (m) |
|---|---|---|---|---|---|
| 1 | 50.8 | 60.3 | 60 | 31.6 | 0.195 |
| 2 | 50.8 | 60.3 | 75 | 39.5 | 0.195 |
| 3 | 31.8 | 42.1 | 45 | 16.5 | 0.195 |
| 4 | 50.8 | 60.3 | 45 | 23.7 | 0.195 |
| 5 | 50.8 | 60.3 | 45 | 23.7 | 0.10 |
| 6 | 76.2 | 88.9 | 45 | 34.9 | 0.195 |
| 7 | 50.8 | 60.3 | 90 | 47.4 | 0.195 |

TABLE III

SOIL PROPERTIES.

| Soil type | Bulk density | Specific surface area | Clay content |
|---|---|---|---|
| Fine Sand | 1.49 g/cm$^3$ | <1 m$^2$/g | 0% |
| Pullman Ap Clay Loam | 1.21 g/cm$^3$ | 249 m$^2$/g | 39.4% |

We claim:

1. An apparatus for determining soil water content and bulk electrical conductivity, the apparatus comprising a time domain-based device, either time domain reflectometry (TDR) or time domain transmission (TDT), the apparatus comprising:
   a) a hollow, substantially cylindrical tube comprising an exterior and interior surface with upper and lower ends, said tube constructed at least in part from a non-conductive material;
   b) at least two electrodes mounted longitudinally onto said exterior surface of said tube, one of said electrodes adapted to transmit an electronic pulse therethrough and designated a voltage electrode, and the other electrode(s) comprising ground electrodes, the electrodes being in communication with a TDR or TDT circuit;
   c) an electronic pulse generator in communication with said voltage electrode effective for transmitting an electronic pulse therethrough;
   d) a voltage receiver in communication with said voltage electrode effective for receiving a reflected pulse therefrom.

2. The apparatus of claim 1 wherein said tube consists essentially of said non-conductive material.

3. The apparatus of claim 1 further comprising a removable auger disposed in the hollow interior of said tube, said auger being effective for cutting a hole into the ground when said lower end of said tube is contacted therewith.

4. The apparatus of claim 1 further comprising a temperature sensor mounted onto said tube effective for measuring soil temperature.

5. The apparatus of claim 1 wherein said tube is constructed from two or more tube segments adapted to be joined together.

6. The apparatus of claim 5 wherein said tube segment comprises two or more waveguides installed longitudinally further wherein each said waveguide comprises said at least two electrodes.

7. The apparatus of claim 1 further comprising a circuit board comprising said electronic pulse generator and said voltage receiver thereon.

8. The apparatus of claim 6 wherein said circuit board is adapted to determine the soil water content and bulk electrical conductivity from said reflected pulse.

9. The apparatus of claim 1 comprising at least three of said electrodes.

10. A method for determining the water content and bulk electrical conductivity of soil comprising:
    a) providing a time domain reflectometry or time domain transmission sensor comprising:
       1) a hollow, substantially cylindrical tube comprising an exterior and interior surface with upper and lower ends, said tube constructed at least in part from a non-conductive material;
       2) at least two electrodes mounted longitudinally onto said exterior surface of said tube, one of said electrodes adapted to transmit an electronic pulse therethrough and designated a voltage electrode, and the other electrodes comprising ground electrodes;
       3) an electronic pulse generator in communication with said voltage electrode effective for transmitting an electronic pulse therethrough; and
       4) a voltage receiver in communication with said voltage electrode effective for receiving a reflected or transmitted pulse therefrom;
    b) embedding said sensor in said soil with said electrodes in contact therewith;
    c) transmitting an electronic pulse from said electronic pulse generator through said voltage electrode;
    d) receiving a reflected or transmitted pulse from said voltage electrode by said voltage receiver;
    e) calculating the reflection coefficient for multiple times such that a waveform of reflection or transmission coefficient values versus travel time is constructed;
    f) determining the pulse travel time through said voltage electrode by analyzing the waveform;
    g) determining the effective frequency of the pulse;
    h) determining the soil bulk permittivity from the effective permittivity;
    i) determining the bulk electrical conductivity;
    j) calculating the soil water content from the travel time, bulk electrical conductivity, temperature and effective frequency.

11. The method of claim 10 by which the waveform is analyzed using an algorithm comprising:
    a) fitting a quadratic equation to the waveform of reflection coefficients comprising a number of data points prior in time and a number of data points later in time to the observed first time of Vmin to the observed last time of Vmin, and taking the derivative of the quadratic equation and solving for the time at which the minimum in the equation occurs.

12. The method of claim 10 wherein said determining the soil bulk permittivity comprises using a mixing model in terms of tube inside and outside diameter and dielectric characteristics.

13. The method of claim 10 wherein said calculating the soil water content comprises one or more calibration methods utilizing combinations of the travel time, bulk electrical conductivity, temperature and effective frequency.

* * * * *